United States Patent
Ohashi et al.

(10) Patent No.: US 8,637,427 B2
(45) Date of Patent: Jan. 28, 2014

(54) ADSORPTIVE COMPOSITION AND ADSORPTIVE MOLDED ARTICLE

(75) Inventors: Kazuaki Ohashi, Kanagawa (JP); Anzu Kasai, Kanagawa (JP); Daisuke Hiratsuka, Osaka (JP); Shigeru Suzuki, Osaka (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 69 days.

(21) Appl. No.: 12/918,582

(22) PCT Filed: Feb. 26, 2009

(86) PCT No.: PCT/JP2009/053558
§ 371 (c)(1),
(2), (4) Date: Aug. 20, 2010

(87) PCT Pub. No.: WO2009/107720
PCT Pub. Date: Sep. 3, 2009

(65) Prior Publication Data
US 2011/0028313 A1    Feb. 3, 2011

(30) Foreign Application Priority Data
Feb. 29, 2008 (JP) ................................. 2008-050984

(51) Int. Cl.
*B01J 20/26* (2006.01)
*B01J 20/02* (2006.01)

(52) U.S. Cl.
USPC ............................. 502/402; 502/400; 502/401

(58) Field of Classification Search
USPC .......................................... 502/400, 401, 402
See application file for complete search history.

(56) References Cited

U.S. PATENT DOCUMENTS

| | | | |
|---|---|---|---|
| 6,358,611 | B1 | 3/2002 | Nagasawa et al. |
| 6,720,006 | B2 | 4/2004 | Hanke et al. |
| 6,822,034 | B2 | 11/2004 | Hanke et al. |
| 2002/0082340 | A1 | 6/2002 | Hanke et al. |
| 2002/0122832 | A1 | 9/2002 | Hanke et al. |
| 2005/0265940 | A1 | 12/2005 | Okada |
| 2010/0010130 | A1 | 1/2010 | Ohashi et al. |

FOREIGN PATENT DOCUMENTS

| | | | |
|---|---|---|---|
| EP | 1066825 | 1/2001 | |
| EP | 1452188 | 9/2004 | |
| EP | 1882511 | 1/2008 | |
| JP | 1-156053 | 6/1989 | |
| JP | 9-75434 | 3/1997 | |
| JP | 10-183207 | 7/1998 | |
| JP | 2002-126511 | 5/2002 | |
| JP | 2006-109902 | * 4/2006 | ............... A61L 9/01 |
| JP | 2006-348213 | 12/2006 | |
| WO | 03/045449 | 6/2003 | |
| WO | 2006/080319 | 8/2006 | |
| WO | 2008/029932 | 3/2008 | |

OTHER PUBLICATIONS

Search report from E.P.O. that issued with respect to patent family member European Patent Application No. 09716152.5, mail date is Jul. 28, 2011.

* cited by examiner

*Primary Examiner* — Stuart Hendrickson
*Assistant Examiner* — Daniel Berns
(74) *Attorney, Agent, or Firm* — Greenblum & Bernstein, P.L.C.

(57) ABSTRACT

An adsorptive composition comprising a composition that contains at least one kind of fatty acid metal salt of any one of Ni, Cu or Co and ultrafine metal particles having a plasmon absorption over 300 to 700 nm. The adsorptive composition has an excellent effect of adsorbing both amine-type smelling components and sulfur-containing smelling components.

2 Claims, No Drawings

US 8,637,427 B2

ADSORPTIVE COMPOSITION AND ADSORPTIVE MOLDED ARTICLE

TECHNICAL FIELD

This invention relates to an adsorptive composition containing a fatty acid metal salt. More specifically, the invention relates to an adsorptive composition capable of adsorbing smelling components of either amine-type smelling components or sulfur-containing smelling components, and to an adsorptive molded article.

BACKGROUND ART

There have heretofore been proposed a variety of deodorizing substances for use being added to thermoplastic resins to impart deodorizing function to the molded articles thereof.

For instance, active carbon, inorganic filler such as porous zeolite or sepiolite, and titanium oxide utilizing photo-catalytic action, are capable of deodorizing a wide range of smelling components and have heat resistance lending themselves well for being melt-kneaded with the thermoplastic resin (patent document 1).

There has, further, been proposed a deodorant using ultrafine metal particles, such as a deodorant using, as an effective component, a colloidal solution of ultrafine metal particles obtained by reducing a metal ion-containing solution (patent document 2).

Further, the present applicant has proposed a resin molded article in which are dispersed ultrafine metal particles having an average particle diameter of 1 to 100 nm by heat-molding a mixture of a fatty acid silver salt or a fatty acid gold salt and a resin at a temperature higher than a temperature at which the fatty acid metal salt starts thermally decomposing but at a temperature lower than a temperature at which the resin thermally deteriorates (patent document 3). The applicant has, further, discovered that the ultrafine metal particles exhibit performance for adsorbing offensively smelling components such as methyl mercaptane, etc. and volatile organic compounds (hereinafter "VOC") such as formaldehyde, etc. (patent document 4).

Patent document 1: JP-A-9-75434
Patent document 2: JP-A-2006-109902
Patent document 3: JP-A-2006-348213
Patent document 4: WO2006/080319

DISCLOSURE OF THE INVENTION

Problems that the Invention is to Solve

However, the deodorants utilizing a porous substance exhibit their deodorizing effect upon adsorbing smelling components, and are accompanied by a problem in that their deodorizing effect extinguishes if the adsorption sites are saturated. Further, in order to improve dispersion property, the inorganic filler must use a dispersant at the time when it is melt-kneaded with a thermoplastic resin. Therefore, there remains a problem in that the adsorption sites in the surfaces of the inorganic filler are covered with the resin or the dispersant causing the deodorizing effect to decrease conspicuously.

Further, the deodorant utilizing the photo-catalytic action has a problem in that the surface of the titanium oxide must have been irradiated with ultraviolet rays at all times to decompose and deodorize the smelling components.

Moreover, ultrafine metal particles and, particularly, the adsorptive ultrafine particles containing ultrafine silver particles, exhibit excellent adsorption performance for methyl mercaptane and sulfur-containing offensively smelling components, such as hydrogen sulfide and methyl sulfide, but are not still satisfactory with regard to adsorbing amine-type offensively smelling components, such as dimethylamine and trimethylamine.

It is, therefore, an object of the present invention to provide an adsorptive composition which exhibits excellent adsorption effect for either the amine-type smelling components or the sulfur-containing smelling components free from the above-mentioned problems possessed by the conventional deodorants.

Another object of the present invention is to provide an adsorptive molded article capable of adsorbing not only sulfur-containing smelling components but also amine-type smelling components such as trimethylamine, and having a very excellent effect for deodorizing offensively smelling components.

Means for Solving the Problems

According to the present invention, there is provided an adsorptive composition comprising a composition that contains at least one kind of fatty acid metal salt of any one of Ni, Cu or Co and ultrafine metal particles having a plasmon absorption from 300 to 700 nm.

In the adsorptive composition of the present invention, it is desired that:
1. The fatty acid metal salt and the ultrafine metal particles are contained in a resin or in a solution;
2. The ultrafine metal particles have an infrared absorption peak near 1518 $cm^{-1}$ stemming from the bond between the organic acid and the metal;
3. The ultrafine metal particles have an average particle diameter of 1 to 100 nm; and
4. The ultrafine metal particles comprise silver.

According to the present invention, further, there is provided an adsorptive molded article having a layer containing at least one kind of fatty acid metal salt of any one of Ni, Cu or Co and a layer in which are dispersed ultrafine metal particles having a plasmon absorption ever from 300 to 700 nm.

In the adsorptive molded article of the present invention, it is desired that:
1. The ultrafine metal particles have an infrared absorption peak near 1518 $cm^{-1}$ stemming from the bond between the organic acid and the metal;
2. The ultrafine metal particles have an average particle diameter of 1 to 100 nm; and
3. The ultrafine metal particles comprise silver.

As described above, the present inventors have discovered that ultrafine metal particles such as of silver have excellent adsorption performance. Though the ultrafine silver particles exhibit performance for adsorbing sulfur-containing components such as methyl mercaptane and the like which are representative offensively smelling components, however, they are not capable of effectively adsorbing amine-type smelling components.

Upon containing a fatty acid metal salt of at least any one of Ni, Cu or Co, however, the adsorptive composition of the present invention becomes capable of effectively adsorbing amine-type smelling components.

The above action and effect of the invention will also become obvious from the results of Examples appearing later. That is, the one obtained by blending copper stearate with silver stearate (Example 1), the one obtained by blending cobalt stearate with silver stearate (Example 2) and a laminated film obtained by laminating a film of a composition containing silver stearate on a film of a composition containing copper stearate (Example 3), all work to deodorize amine-type smelling components and sulfur-type smelling components such as methyl mercaptane, and are, therefore, capable of effectively deodorizing offensively smelling components.

On the other hand, when use is made of a metal stearate comprising silver, manganese or zinc as a metal component, the amine-type smelling components can be deodorized up to a maximum of only 30% (Comparative Examples 1 to 4).

Effects of the Invention

The adsorptive composition of the present invention effectively adsorbs amine-type smelling components due to the fatty acid metal salt of Ni, Cu or Co and effectively adsorbs sulfur-containing smelling components due to the fine metal particles having a plasmon absorption ever from 300 to 700 nm.

By molding an article having a layer containing at least one kind of fatty acid metal salt of any one of Ni, Cu or Co and a layer in which are dispersed ultrafine metal particles having a plasmon absorption over 300 to 700 nm, further, offensively smelling components of both amine-type smelling components an sulfur-type smelling components can be deodorized more effectively.

MODE FOR CARRYING OUT THE INVENTION (Fatty Acid Metal Salts)

The metals of the fatty acid metal salts for effectively adsorbing amine-type smelling components used in the invention are Co, Cu and Ni as described above. Among them, Co and Cu are desired.

The fatty acid used for the fatty acid metal salt of the invention is a fatty acid having 3 to 30 carbon atoms and may be either saturated or unsaturated. Examples thereof include caproic acid, caprylic acid, capric acid, lauric acid, myristic acid, palmytic acid, oleic acid, linoleic acid, linolenic acid, stearic acid and arachidinic acid. Particularly, stearic acid and myristic acid are desired. Upon having a branch and an increased number of carbons, the fatty acid by itself is capable of adsorbing smelling components making it possible to further improve the deodorizing effect. A plurality of number of fatty acids may be used.

Desirably, there is used a straight-chain saturated fatty acid having 12 to 22 carbon atoms. If the number of carbon atoms is less than 12, the fatty acid highly dissolves in water decreasing the yield of the fatty acid metal salt which is the product. If the number of carbon atoms is not less than 23, the fatty acid dissolves less in water which is the starting material making it difficult to prepare the fatty acid metal salt.

In the present invention, in particular, it is desired to use a fatty acid metal salt having a water content of less than 200 ppm. Upon mixing it with the resin and heat-molding the mixture, therefore, there is obtained a resin composition having a favorable color tone and particularly excellent ability for adsorbing offensively smelling substances.

As the ultrafine metal particles having a plasmon absorption from 300 to 700 nm capable of effectively adsorbing sulfur-type smelling components, further, there can be exemplified Ag, Au, In, Pd, Pt, Fe, Nb, Ru, Rh and Sn. Among them, Ag is particularly desired. These metal components may be used in a single kind, as a mixture or as an alloy.

For these fatty acid metal salts, too, it is desired to use the same fatty acid components as those for the above-mentioned fatty acid metal salts.

In the present invention, in particular, it is desired to use fatty acid silver. This enables the formation of ultrafine metal particles having a bond between the fatty acid and the metal in the resin or in the coating at the time of heating such as molding or firing the coating, making it possible to excellently adsorb sulfur-type smelling components.

It is desired that the ultrafine metal particles have a maximum diameter of not larger than 1 μm and an average particle diameter, particularly, in a range of 1 to 100 nm.

The average particle diameter referred to in this specification is an average value of the individual metal particles assuming that there is no gap among the metal particles.

In the present invention, it can be confirmed that the ultrafine metal particles have an effect of adsorbing the sulfur-type smelling components from the phenomenon of plasmon absorption in that the ultrafine metal particles absorb light of wavelengths over a range of 300 to 700 nm.

The above ultrafine metal particles are the adsorptive ultrafine metal particles having an infrared ray absorption peak near 1518 $cm^{-1}$ stemming from the bond between the organic acid and the metal, having high surface activity and large surface areas, having excellent reactivity to the sulfur-type smelling components such as methyl mercaptane, higher adsorption rate and larger adsorption amount than those of the ordinary particles, and expressing excellent adsorption effect. Moreover, due to the presence of organic acid on the surfaces of the ultrafine metal particles, the ultrafine metal particles are very favorably dispersed in the resin and, at the same time, effectively suppress the decomposition of the resin, preventing a decrease in the molecular weight of the resin so that the moldability will not be impaired.

(Adsorptive Resin Compositions)

The adsorptive composition of the present invention can be a resin composition containing, in a resin, at least one kind of fatty acid metal salt of any one of Ni, Cu or Co and ultrafine metal particles having a plasmon absorption from 300 to 700 nm. Upon heat-molding the resin composition, there can be obtained an adsorptive molded article of a desired form.

As the resin to be blended with the fatty acid metal salt, there can be used any known thermoplastic resin that can be melt-molded, like olefin resins such as low-, intermediate- or high-density polyethylene, linear low-density polyethylene, linear ultra-low-density polyethylene, isotactic polypropylene, syndiotactic polypropylene, propylene/ethylene copolymer, polybutene-1, ethylene/butene-1 copolymer, propylene/butene-1 copolymer and ethylene/propylene/butene-1 copolymer; polyester resins such as polyethylene terephthalate, polybutylene terephthalate and polyethylene naphthalate; polyamide resins such as nylon 6, nylon 6,6 and nylon 6,10; and polycarbonate resin.

In the adsorptive resin composition of the present invention, it is desired that the resin has an oxygen permeability coefficient of not less than $1.0 \times 10^{-4}$ cc·m/m²·day·atm. This makes it possible to easily adsorb smelling components and to further improve deodorizing performance.

According to the present invention, it is particularly desired to use a polyethylene for the adsorptive resin composition.

Depending on the use, further, the adsorptive resin composition of the present invention can be blended with various blending agents that have been known per se. such as filler, plasticizer, leveling agent, viscosity-imparting agent, viscosity-reducing agent, stabilizer, antioxidant and ultraviolet ray absorber according to known recipe.

It is desired that the adsorptive resin composition of the present invention is blended with the fatty acid metal salt of any one of Co, Cu or Ni in an amount of 0.01 to 10 parts by weight per 100 parts by weight of the resin. If the amount is smaller than the above range, the adsorptive effect is not obtained to a sufficient degree. If the amount is larger than the above range, on the other hand, the moldability may decrease, which is not desirable.

It is, further, desired that the fatty acid metal salt of Co, Cu or Ni used for the adsorptive resin composition is in the form of fine particles having an average particle diameter of 1 to 100 μm, and is kneaded with the resin.

On the other hand, the other fatty acid metal salt such as fatty acid silver used for forming ultrafine metal particles having a plasmon absorption is added desirably in an amount of 0.01 to 10 parts by weight per 100 parts by weight of the resin, and the obtained ultrafine metal particles desirably have an average particle diameter of 1 to 100 nm.

The adsorptive resin composition of the invention can be subjected to a known melt molding such as two-roll method, injection molding, extrusion molding or compression molding to finally obtain the adsorptive resin-molded articles in shapes that meet the use, such as granules, pellets, films, sheets, containers, etc.

The conditions for heat-treating the resin composition vary depending on the kinds of the resin and the fatty acid metal salt that are used, and cannot be definitely defined. It is, however, desired that the resin composition is heat-treated at a temperature at which the fatty acid metal salt that forms the ultrafine metal particles having a plasmon absorption undergoes the thermal decomposition in the resin but at which the resin is not thermally deteriorated.

The temperature at which the fatty acid metal salt undergoes the thermal decomposition may be higher than a temperature at which the fatty acid metal salt starts decomposing but does not necessarily have to be higher than the temperature at which the fatty acid metal salt starts decomposing. In practice, the temperature is affected by the heat of shearing due to the screw or by the residence time in addition to the setpoint temperature of the extruder. It is, therefore, desired to conduct the heat treatment by adjusting the working conditions such as residence time, heating time, rotational speed of the screw, etc.

Further, the adsorptive molded article comprising the adsorptive resin composition of the invention may by itself constitute an adsorptive resin molded article but may also assume a multi-layer structure including a layer that contains at least one kind of fatty acid metal salt of any one of Ni, Cu or Co and a layer in which are dispersed ultrafine metal particles having a plasmon absorption from 300 to 700 nm. As the ultrafine metal particles having a plasmon absorption from 300 to 700 nm, there can be exemplified Ag, Au and Cu, and Ag is particularly desirable.

The resin molded article obtained from the adsorptive resin composition of the invention has excellent deodorizing performance, exhibits adsorption performance just as the resin is molded into an article, and excels in productivity.

(Adsorptive Coating Compositions)

The adsorptive composition of the present invention can be a coating composition containing, in a coating material, at least one kind of fatty acid metal salt of any one of Ni, Cu or Co and ultrafine metal particles having a plasmon absorption from 300 to 700 nm, which is capable of forming a coating. The coating composition is applied onto the base body and is fired to form an adsorptive coating on the base body.

It is desired that the fatty acid metal salt of Ni, Cu or Co is added in an amount of 0.01 to 10 parts by weight per 100 parts by weight of the coating component (resin component). If the amount thereof is smaller than the above range, the deodorizing effect is not obtained to a sufficient degree. If the amount thereof is larger than the above range, on the other hand, the coating formability may decrease, which is not desirable.

Like in the case of the above resin composition, further, a fatty acid metal salt such as fatty acid silver is added to form ultrafine metal particles having the plasmon absorption so that the coating expresses the above-mentioned effect.

As the fatty acid metal salt such as the fatty acid silver, etc. like in the above resin composition, it is desired that the other fatty acid metal salt is added in an amount of 0.01 to 10 parts by weight per 100 parts by weight of the coating component (resin component).

As the coating component to which the fatty acid metal salt is to be added, there can be used various components provided they are capable of forming a coating upon heating. For example, though not limited thereto only, there can be used a known coating composition such as acrylic coating material, epoxy coating material, phenol coating material, urethane coating material, polyester coating material or alkyd resin coating material.

The conditions for heat-treating the coating composition vary depending upon the kinds of the coating component and the fatty acid metal salt that are used, and cannot be definitely defined. The coating composition, however, must be heat-treated under the conditions of a temperature range in which the fatty acid metal salt for forming the ultrafine metal particles having the plasmon absorption undergoes the thermal decomposition in the coating material but in which the coating component is not thermally deteriorated for 60 to 600 seconds.

The coating obtained from the adsorptive coating composition of the invention has excellent deodorizing performance, exhibits adsorption performance just as the coating is formed, and excels in productivity.

(Adsorptive Dispersion Solutions)

The adsorptive composition of the invention can be an adsorptive dispersion solution containing, in a dispersion medium, at least one kind of a fatty acid metal salt of any one of Ni, Cu or Co and ultrafine metal particles having a plasmon absorption of from 300 to 700 nm.

The adsorptive dispersion solution can be used by being sprayed or applied onto, or having been soaked in, the dwelling-related members such as floors, walls, curtains, carpets, etc., fibrous products such as of air conditions, woven fabrics, nonwoven fabrics, etc., and the filtering members such as masks, filters, etc.

As the dispersion medium used for the adsorptive dispersion solution of the invention, a polyhydric alcohol can be favorably used. It is desired that the polyhydric alcohol has a boiling point higher than a temperature at which the fatty acid metal salt undergoes the thermal decomposition in the dispersion medium, and its examples include polyethylene glycol, diethylene glycol and glycerol. Here, however, the polyethylene glycol is particularly preferably used.

The polyethylene glycol preferably has an average molecular weight in a range of 200 to 20000 and, particularly preferably, 400 to 10000. Further, a plurality of kinds of polyethylene glycols having different molecular weights may be used being mixed together.

In the adsorptive dispersion solution of the invention, it is desired that the fatty acid metal salt of Ni, Cu or Co is added to the dispersion medium in an amount of 0.1 to 20% by weight and, particularly, 1 to 5% by weight. If the amount of the fatty acid metal salt is smaller than the above range, the adsorption performance is not attained to a sufficient degree. If the amount thereof is larger than the above range, on the other hand, the dispersion thereof may decrease, which is not desirable.

It is, further, desired that the fatty acid metal salt such as fatty acid silver for forming ultrafine metal particles having the plasmon adsorption is added in an amount of 0.01 to 5% by weight.

Desirably, further, an antioxidant is added as a protection agent. Addition of the antioxidant prevents the thermal deterioration at the time of heating.

As the antioxidant to be used, though not limited thereto only, there can be exemplified known ones such as tocopherols (vitamin E), hindered phenol-type antioxidant, phosphorus-type antioxidant and ethylene bisstearic acid amide. Particularly desirably, Irganox 1010 (registered trade mark, produced by Chiba Specialty Chemicals Co.) can be used. The antioxidant is desirably added to the dispersion medium in an amount of 0.01 to 20% by weight.

The dispersion solution of the present invention can be prepared by adding, to a dispersion medium, the fatty acid metal salt of any one of Co, Cu or Ni, the fatty acid metal salt for forming ultrafine metal particles having the plasmon absorption and, as required, an antioxidant, and stirring and mixing them together while heating them at a temperature at which the fatty acid metal salt for forming the ultrafine metal particles having the plasmon absorption undergoes the thermal decomposition in the dispersion medium but lower than the boiling point of the solution. The heating time differs depending upon the kind of the dispersion medium that is used and the amount of the metal organoate that is added, and cannot be definitely defined, but is desirably 1 to 1800 seconds and, particularly, 5 to 300 seconds. After heated and mixed, the dispersion solution is cooled down to room temperature and is filtered. Thus, the free fatty acid is removed from the dispersion solution, and the adsorptive dispersion solution of the invention is obtained.

The dispersion solution obtained by the production method of the invention can by itself be used as an adsorptive (deodorant) but is, desirably, used being diluted with a solvent.

The solvent used for the dilution may be, though not limited thereto only, water such as purified water or ion-exchanged water; lower alcohols such as methanol, ethanol, propanol, isopropanol and butanol; general modified alcohols such as those modified with methanol, those modified with benzole, those modified with triol, those modified with methyl ethyl ketone, those modified with denatonium benzoate and those modified with perfume; modified alcohols such as ethylene glycol monoethyl ether, chloroform, diethyl carbonate, ethyl acetate, ethyl propionate, ethyl butyrate, hexane, and ethyl ether for industrial use; and glycol-type solvents such as ethylene glycol monobutyl ether, diethylene glycol monobutyl ether, propylene glycol monomethyl ether, propylene glycol monopropyl ether, propylene glycol monobutyl ether, propylene glycol diethylene glycol monobutyl ether, dipropylene glycol ethylene glycol monobutyl ether, ethylene glycol monophenyl ether, and triethylene glycol monophenyl ether. These solvents may be used alone or in a combination of two or more kinds.

The present invention preferably uses a low-boiling solvent having a boiling point of not higher than 100° C., such as water or ethanol and, particularly preferably uses an aqueous solution containing ethanol at a concentration of 1 to 30%.

EXAMPLES

Calculating the Deodorizing Ratio

1. Measuring the Concentration of Offensively Smelling Substance of When Not Deodorized.

By using a micro syringe, offensively smelling substances, i.e., dimethylamine and methyl mercaptane each in an amount of 5 μL were injected into 500-mL glass bottles purged with a nitrogen gas and sealed for their mouth portions with rubber plugs, so adjusted that their concentrations were 10 ppm, and were left to stand at room temperature (25° C.) for a whole day. After left to stand for a whole day, detector tubes (manufactured by Gas-Tech Co.) were inserted in the bottles to measure the concentrations of the remaining offensively smelling substances, which were regarded as the concentrations (A) of the offensively smelling substances of when not deodorized.

2. Measuring the Concentrations of Offensively Smelling Substances After Deodorized.

A film obtained by blending a thermoplastic resin with a fatty acid metal salt was cut into two square pieces each side measuring 50 mm, and the pieces were hung in the 500-mL glass bottles purged with the nitrogen gas and sealed with the rubber plugs. Next, offensively smelling substances, i.e., dimethylamine and methyl mercaptane each in an amount of 5 μL were injected therein by using the micro syringe so that the concentrations in the bottles were adjusted to be 10 ppm, and were left to stand at room temperature (25° C.) for a whole day. After left to stand for a whole day, the detector tubes (manufactured by Gas-Tech Co.) were inserted in the bottles to measure the concentrations of the remaining offensively smelling substances, which were regarded as the concentrations (B) of the offensively smelling substances after deodorized.

3. Calculating the Ratio of Deodorizing Offensively Smelling Substances.

A value obtained by subtracting the concentration (B) of offensively smelling substances after deodorized from the concentration (A) of offensively smelling substances of when not deodorized, was divided by the concentration (A) of offensively smelling substances, and was expressed as the deodorization ratio in percentage.

1. Confirming the Plasmon Absorption by Using a Spectrophotometer.

The film containing ultrafine metal particles was measured for its absorbance by using a spectrophotometer (UV-3100PC manufactured by Shimazu Seisakusho Co.) to make sure the presence of plasmon absorption of from 300 to 700 nm.

Example 1

A low-density polyethylene resin was blended with copper stearate (II) and silver stearate as fatty acid metal salts each in an amount of 0.5% by weight, and was extruded by using a biaxial extruder at an extrusion-molding temperature of 220° C. to prepare a single-layer film (thickness of 50 μm).

The obtained single-layer film was measured for its spectral transmission factor, and the presence of plasmon absorption and the ratio of deodorizing offensively smelling substances were calculated.

Example 2

A single-layer film was prepared in the same manner as in Example 1 but adding cobalt stearate (II) and silver stearate as fatty acid metal salts each in an amount of 0.5% by weight, and the presence of plasmon absorption and the deodorizing ratio were calculated.

Example 3

A low-density polyethylene resin of a first layer was blended with copper stearate (II) as a fatty acid metal salt, and a low-density polyethylene resin of a second layer was blended with silver stearate as a fatty acid metal salt each in an amount of 0.5% by weight. The two layers were coextruded by using a biaxial extruder at an extrusion-molding temperature of 220° C. to prepare a two-layer film (thickness of 50 µm).

Next, the presence of plasmon absorption and the deodorizing ratio of the film were calculated in the same manner as in Example 1.

Comparative Example 1

Silver stearate was used as the fatty acid metal salt, and the presence of plasmon absorption and the deodorizing ratio were calculated in the same manner as in Example 1.

Comparative Example 2

Manganese stearate (II) was used as the fatty acid metal salt, and the presence of plasmon absorption and the deodorizing ratio were calculated in the same manner as in Example 1.

Comparative Example 3

Zinc stearate (II) was used as the fatty acid metal salt, and the presence of plasmon absorption and the deodorizing ratio were calculated in the same manner as in Example 1.

Comparative Example 4

Manganese stearate (II) was added to the first layer as the fatty acid metal salt in an amount of 0.5% by weight, silver (average particle diameter of 4.5 µm) was added to the second layer in an amount of 0.5% by weight, and the presence of plasmon absorption and the deodorizing ratio were calculated in the same manner as in Example 3.

metal particles having a plasmon absorption from 300 to 700 nm of Examples 1 and 2, and by the laminated film having a layer containing a fatty acid metal salt of any one of Ni, Cu or Co and a layer in which are dispersed ultrafine metal particles having a plasmon absorption over 300 to 700 nm of Example 3.

INDUSTRIAL APPLICABILITY

The adsorptive composition of the present invention is capable of effectively absorbing amine-type smelling components due to the fatty acid metal salt of Ni, Cu or Co and sulfur-containing smelling components due to the ultrafine metal particles having a plasmon absorption of from 300 to 700 nm. The adsorptive composition can be provided in the form of various resin compositions, such as particles, pellets, fibers, films, sheets and containers, or in the form of coating compositions or dispersion solutions, and can be utilized in a variety of industrial fields.

The invention claimed is:

1. A resin composition containing adsorptive ultrafine metal particles, comprising a resin composition that contains at least one kind of fatty acid metal salt of any one of Ni, Cu or Co in a low-density polyethylene and ultrafine silver particles having an average particle diameter of 1 to 100 nm, a plasmon absorption from 300 to 700 nm and an infrared absorption peak at 1518 $cm^{-1}$ stemming from the bond between an organic acid component and a metal, wherein said organic acid is a saturated fatty acid having 3 to 30 carbon atoms, and a silver salt of said organic acid and at least one kind of the fatty acid metal salt of any one Ni, Cu or Co are heated and mixed in the low-density polyethylene to form said ultrafine silver particles and to render the organic acid present on the surfaces of said ultrafine silver particles so that

TABLE 1

|  | | First layer | | Second layer | | Dimethylamine deodorizing ratio | Methyl mercaptane deodorizing ratio | Presence of plasmon absorption |
| --- | --- | --- | --- | --- | --- | --- | --- | --- |
|  | Layer constitution | Base resin | Fatty acid metal salt | Base resin | Fine particles | | | |
| Ex. 1 | single layer | LDPE | *1 *2 | — | — | 80% | 98% | yes |
| Ex. 2 | single layer | LDPE | *3 *2 | — | — | 65% | 98% | yes |
| Ex. 3 | 2 layers | LDPE | *1 | LDPE | *6 | 75% | 98% | yes |
| Comp. Ex. 1 | single layer | LDPE | *2 | — | — | 20% | 98% | yes |
| Comp. Ex. 2 | single layer | LDPE | *4 | — | — | 30% | 10% | no |
| Comp. Ex. 3 | single layer | LDPE | *5 | — | — | 20% | 30% | no |
| Comp. Ex. 4 | 2 layers | LDPE | *4 | LDPE | *7 | 30% | 20% | no |

*1: copper stearate, 0.5 wt %
*2: silver stearate, 0.5 wt %
*3: cobalt stearate, 0.5 wt %
*4: manganese stearate, 0.5 wt %
*5: zinc stearate, 0.5 wt %
*6: silver stearate, 0.5 wt %
*7: silver, 0.5 wt %

It will be learned that excellent deodorizing effects against offensive smells of amines and sulfur-containing smelling components such as methyl mercaptane are expressed by the single-layer films comprising a resin composition containing a fatty acid metal salt of any one of Ni, Cu or Co and ultrafine the ultrafine silver particles and the fatty acid metal salt of any one of Ni, Cu or Co are dispersed in the low-density polyethylene.

2. An adsorptive molded article comprising a layer that contains at least one kind of fatty acid metal salt of any one of Ni, Cu or Co in a low-denstiy polyethylene, and a layer that contains ultrafine silver particles having an average particle diameter of 1 to 100 nm a plasmon absorption at 300 to 700 nm and an infrared absorption peak at 1518 cm$^{-1}$ stemming from the bond between an organic acid component and a metal in the low-density polyethylene, wherein said organic acid is a saturated fatty acid having 3 to 30 carbon atoms, and a silver salt of said organic acid is heated and mixed in the low-density polyethylene to form said ultrafine silver particles and to render the organic acid present on the surfaces of said ultrafine silver particles, and at least one kind of fatty acid metal salt of any one of Ni, Cu or Co is heated and mixed in the low-density polyethylene so as to be dispersed therein.

* * * * *